(12) United States Patent
Mastroianni et al.

(10) Patent No.: US 9,012,661 B2
(45) Date of Patent: *Apr. 21, 2015

(54) ORGANOPHOSPHORUS COMPOUNDS, CATALYTIC SYSTEMS COMPRISING SAID COMPOUNDS AND METHOD OF HYDROCYANATION OR OF HYDROFORMYLATION USING SAID CATALYTIC SYSTEMS

(75) Inventors: Sergio Mastroianni, Lyons (FR); Igor Mikhel, Moscow (RU); Paul Pringle, Bristol Avon (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 88 days.

This patent is subject to a terminal disclaimer.

(21) Appl. No.: 13/256,387

(22) PCT Filed: Mar. 5, 2010

(86) PCT No.: PCT/EP2010/052851
§ 371 (c)(1),
(2), (4) Date: Oct. 18, 2011

(87) PCT Pub. No.: WO2010/102962
PCT Pub. Date: Sep. 16, 2010

(65) Prior Publication Data
US 2012/0035377 A1 Feb. 9, 2012

(30) Foreign Application Priority Data
Mar. 13, 2009 (FR) ...................................... 09 51577

(51) Int. Cl.
*C07D 323/06* (2006.01)
*C07C 45/00* (2006.01)
*C07C 253/00* (2006.01)
*C07B 41/06* (2006.01)
*C07F 9/6571* (2006.01)
*C07B 43/08* (2006.01)
*C07C 45/50* (2006.01)

(52) U.S. Cl.
CPC .............. *C07F 9/6571* (2013.01); *C07B 41/06* (2013.01); *C07B 43/08* (2013.01); *C07C 45/50* (2013.01)

(58) Field of Classification Search
CPC ........ C07C 45/50; C07B 43/08; C07F 9/6571
See application file for complete search history.

(56) References Cited

U.S. PATENT DOCUMENTS

| 3,583,943 A | 6/1971 | Weber et al. |
| 7,495,133 B2 | 2/2009 | Borgmann et al. |
| 8,546,589 B2 * | 10/2013 | Mastroianni et al. ......... 549/212 |

FOREIGN PATENT DOCUMENTS

| FR | 1599761 | 8/1970 |
| WO | 98/42717 A1 | 10/1998 |

OTHER PUBLICATIONS

Baber, R.A., et al. "Phenylphosphatrioxa-adamantanes: bulky, robust, electron-poor ligands that give very efficient rhodium(I) hydroformylation catalysts." Journal of the Royal Society of Chemistry. (2005), pp. 1079-1085.*
American Chemical Society (ACS). STN Chemical Abstract Service (CAS). RN database entry 108019-87-0. © May 9, 1987.*
Pugh, "Phospha-adamantanes: A New Class of Bulky Alkyl Phosphine Ligands," Thesis for Doctor of Philosophy in Chemistry, 2000, pp. i-238.
van Leeuwen et al, "Ligand Bite Angle Effects in Metal-catalyzed C-C Bond Formation," Chem. Rev., 2000, pp. 2741-2769, vol. 100.
Baber et al, "Phenylphosphatrioxa-adamantanes: bulky, robust, electron-poor ligands that give very efficient rhodium(I) hydroformylation catalysts," Dalton Trans., 2005, pp. 1079-1085.
Epstein et al., "A Novel Phosphorus Heterocyclic System from the Reactions of Phosphine and Primary Phosphines with 2,4-Pentanedione," J. Am. Chem. Soc., 1961, pp. 3279-3282, vol. 83.
Downing et al., "General Routes to Alkyl Phosphatrioxaadamantane Ligands," Organometallics, 2008, pp. 3216-3224, vol. 27.
International Search Report issued on Jul. 22, 2010, by the European Patent Office as the International Searching authority in corresponding International Patent Application No. PCT/EP2010/052851.
Written Opinion of the International Searching Authority issued on Sep. 13, 2011, in corresponding International Patent Application No. PCT/EP2010/052851.
Jonathan Paul Hopewell, "New Directions in Phospha-adamantane", Thesis submitted to the University of Bristol in accordance with the requirements of the degree of doctor of philosophy in the school of chemistry, Aug. 2009, pp. 1-187, Faculty of Science, University of Bristol.
Jonathan Paul Hopewell, "Phospha-adamantane Cage Ligands: Their Resolution, Organometallic Chemistry and Applications in Catalysis", 2008 Student Conference Applied Catalysis: Towards Sustainable Chemical Industry, Nov. 2008.

* cited by examiner

*Primary Examiner* — Andrew D Kosar
*Assistant Examiner* — John S Kenyon
(74) *Attorney, Agent, or Firm* — Robert B. Furr, Jr.

(57) ABSTRACT

Organophosphorus compounds, catalytic systems comprising a metallic element forming a complex with the organophosphorus compounds and methods of hydrocyanation and of hydroformylation employed in the presence of the catalytic systems are described.

23 Claims, No Drawings

ORGANOPHOSPHORUS COMPOUNDS, CATALYTIC SYSTEMS COMPRISING SAID COMPOUNDS AND METHOD OF HYDROCYANATION OR OF HYDROFORMYLATION USING SAID CATALYTIC SYSTEMS

CROSS-REFERENCE TO PRIOR APPLICATIONS

This application is the United States national phase of PCT/EP2010/052851, filed Mar. 5, 2010, and designating the United States (published in the French language on Sep. 16, 2010, as WO 2010/102962 A1; the title and abstract were also published in English) and claims priority under 35 U.S.C. §119 of FR 0951577, filed Mar. 13, 2009, each hereby expressly incorporated by reference in its entirety and each assigned to the assignee hereof.

The present invention relates to organophosphorus compounds, their use in catalytic systems and methods of synthesis of organic compounds using said catalytic systems, notably the methods of hydrocyanation of ethylenically unsaturated organic compounds to compounds comprising at least one nitrile function and the methods of hydroformylation of unsaturated compounds for the manufacture of aldehydes.

The reaction of hydrocyanation is, for example, described in French patent 1 599 761 which relates to a method of preparation of nitriles by addition of hydrocyanic acid to organic compounds having at least one ethylenic double bond, in the presence of a catalyst comprising nickel and an organophosphorus ligand, a triarylphosphite. This reaction can be carried out in the presence or absence of a solvent.

When a solvent is used, it is preferably a hydrocarbon, such as benzene or xylenes or a nitrile such as acetonitrile.

The catalyst employed is an organic nickel complex, containing ligands such as phosphines, arsines, stibines, phosphites, arsenites or antimonites.

The presence of a promoter for activating the catalyst, such as a boron compound or a metal salt, generally a Lewis acid, is also recommended in said patent.

Numerous other catalytic systems have been proposed, generally comprising organophosphorus compounds belonging to the family of the phosphites, phosphonites, phosphinites and phosphines. These organophosphorus compounds can comprise one phosphorus atom per molecule and are described as monodentate ligands, or several phosphorus atoms per molecule, which are then called multidentate ligands. More particularly, numerous ligands containing two phosphorus atoms per molecule (bidentate ligand) have been described in numerous patents.

However, new catalytic systems with better performance both with respect to catalytic activity and with respect to stability are always being sought for improving the general economics of the method.

The reaction of hydroformylation, which consists of reacting an olefinic compound with a mixture of carbon monoxide and hydrogen under pressure to form an aldehyde, is also described in numerous documents. For example, a general account of the hydroformylation of olefins can be found in B. Cornils and W. A. Herrmann (Eds.), *Applied Homogeneous Catalysis with Organometallic Compounds*, Vol. 1 and 2, Weinheim, 1996 and in the article by E. KUNTZ published in the encyclopaedia "Les Techniques de l'Ingénieur" J 5 750-1, 2002 edition. The catalytic systems used in this reaction generally comprise carbonyl hydrides of cobalt or rhodium, which can be complexed by an organophosphorus ligand, notably organophosphines such as triphenylphosphine or organophosphites. A general description of the catalytic systems used in the hydroformylation of alkenes is given in U.S. Pat. No. 7,495,133. Just as for hydrocyanation, new catalytic systems are being sought for improving the properties of the method both with respect to the performance of the catalyst and with respect to simplification of the method.

One of the aims of the present invention is to propose a novel family of ligands which makes it possible to obtain, with transition metals, catalytic systems displaying good catalytic activity notably in the reactions of hydrocyanation and hydroformylation.

For this purpose, the present invention proposes organophosphorus compounds, characterized in that said organophosphorus compounds correspond to one of the general formulae (I) and (II):

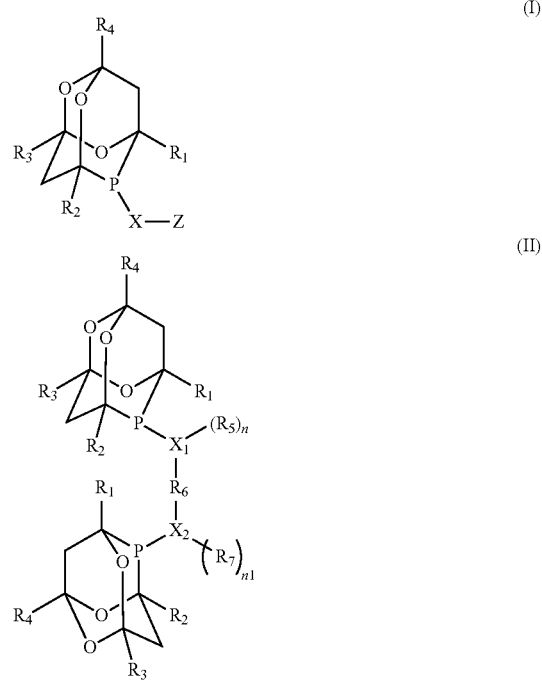

in which:
R$_1$, R$_2$, R$_3$, R$_4$, R$_5$, R$_7$ and Z, which may be identical or different, represent a hydrogen atom, a linear or branched alkyl radical having from 1 to 12 carbons which can contain heteroatoms, a radical comprising a substituted or unsubstituted aromatic or cycloaliphatic radical which can comprise heteroatoms, a carbonyl, alkoxycarbonyl or alkoxy radical, a halogen atom, a nitrile group or a haloalkyl group having 1 to 12 carbon atoms X, X1 and X2, which may be identical or different, represent an oxygen, nitrogen, sulphur, carbon or silicon atom R$_6$ represents a covalent bond, a linear or branched aliphatic radical, a radical comprising a substituted or unsubstituted aromatic or cycloaliphatic ring or several aromatic rings, condensed or joined together by a bond n and n1, which may be identical or different, are integers respectively equal to the valency of elements X$_1$, X$_2$ reduced by 2.

According to a particular embodiment of the invention, these organophosphorus compounds belong to the family of organophosphinites and correspond to one of the general formulae (III) and (IV):

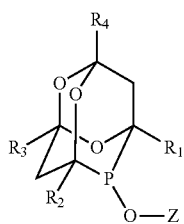
(III)

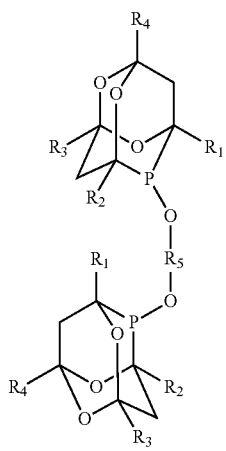
(IV)

in which:

R₁, R₂, R₃, R₄, which may be identical or different, represent a hydrogen atom, a linear or branched alkyl radical having from 1 to 12 carbon atoms which can contain heteroatoms, Z represents a substituted or unsubstituted aromatic or cycloaliphatic radical which can comprise heteroatoms, a carbonyl, alkoxycarbonyl or alkoxy radical, a halogen atom, a nitrile group or a haloalkyl group having 1 to 12 carbon atoms, R₅ represents a covalent bond, a linear or branched aliphatic radical, a radical comprising a substituted or unsubstituted aromatic or cycloaliphatic ring or, several aromatic rings, condensed or joined together by a bond.

As preferred compounds of general formulae (I), (II), (III) or (IV) of the invention, we may mention the compounds of the following formulae:

ligand 1

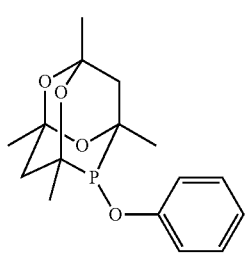

ligand 2

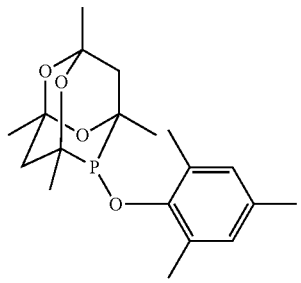

ligand 3

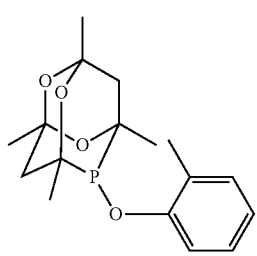

ligand 4 ligand 5 ligand 6

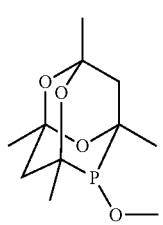

ligand 7

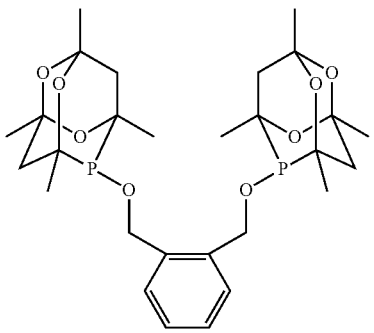

ligand 8

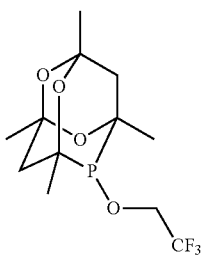

ligand 9

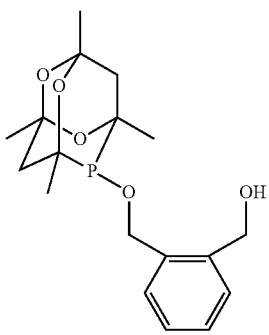

ligand 10

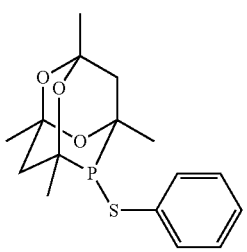

These compounds can be prepared from compounds called hereinafter CgPH of the following formula:

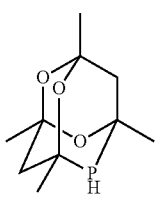

These CgPH compounds are described in the scientific article published in the journal ORGANOMETALLICS Vol. 27, No. 13 p. 3215-3224 of 2008: "General Routes to Alkyl Phosphotrioadamantane Ligands" by Joanne H. Downing et al., as well as their method of synthesis.

The CgPH compounds are transformed to CgPX compounds, in which X represents a halogen atom, preferably bromine, by reaction with the molecular halogen in an organic solvent such as dichloromethane.

The CgPX compounds are then reacted for example with a compound obtained by reaction of a hydroxylated compound corresponding to the residue Z or R5 in general formulae III and IV with an organoalkali metal compound, preferably organolithium compound, in a solvent such as tetrahydrofuran.

Details and additional information on the methods of manufacture of the compounds of formulae I and II will be given in the examples presented below.

According to another object of the invention, the organophosphorus compounds of formulae (I), (II), (III) or (IV) are used for the manufacture of catalytic systems by combining with a metallic element to form a complex. Overall, the composition of these catalytic systems can be represented by general formula (V) or (VI) (these formulae do not correspond to the structure of the compounds and complexes present in the catalytic system):

$$M[L_f]_t \quad (V)$$

$$HM[L_f]_{t+n}(CO)_{4-n} \quad (VI)$$

in which:

M is a transition metal $L_f$ represents at least one organophosphorus ligand of formula (I), (II), (III) or (IV)

t represents a number between 1 and 10 (inclusive)

n represents a number between 1 and 4 (inclusive)

The metals M that can be complexed are in general all the transition metals of groups 1b, 2b, 3b, 4b, 5b, 6b, 7b and 8 of the periodic system, such as published in "Handbook of Chemistry and Physics, 51st Edition (1970-1971)" by The Chemical Rubber Company.

Among these metals, we may mention more particularly the metals that can be used as catalysts in the reactions of hydrocyanation and of hydroformylation. Thus, we may mention, as non-limiting examples, nickel, cobalt, iron, ruthenium, rhodium, palladium, osmium, iridium, platinum, copper, silver, gold, zinc, cadmium, mercury. Nickel is the preferred element for the hydrocyanation of olefins and unsaturated nitriles and cobalt or rhodium for hydroformylation, notably of the alkenes.

The preparation of the catalytic systems comprising compounds of general formula (I), (II), (III) or (IV) can be carried out by bringing a solution of a compound of the metal selected, for example nickel or rhodium, in contact with a solution of the organophosphorus compound of the invention.

The compound of the metal can be dissolved in a solvent. In the compound employed, the metal can be either at the degree of oxidation that it will have in the organometallic complex, or at a higher degree of oxidation.

As an example, it may be mentioned that in the organometallic complexes of the invention, rhodium is at degree of oxidation (I), ruthenium at degree of oxidation (II), platinum at degree of oxidation (0), palladium at degree of oxidation (0), osmium at degree of oxidation (II), iridium at degree of oxidation (I), nickel at degree of oxidation (0).

If, during preparation of the organometallic complex, the metal is employed at a higher degree of oxidation, it can be reduced in situ.

Among the compounds of metals M that can be used for preparing the organometallic complexes, notably when the metal is nickel, we may mention, as non-limiting examples, the following nickel compounds:

compounds in which nickel is at degree of oxidation zero, such as potassium tetracyanonickelate $K_4[Ni(CN)_4]$, nickel zero bis(acrylonitrile), nickel bis(cyclooctadiene-1,5) (also called $Ni(cod)_2$) and derivatives containing ligands such as tetrakis(triphenyl phosphine) nickel zero.

nickel compounds such as carboxylates (notably acetate), carbonate, bicarbonate, borate, bromide, chloride, citrate, thiocyanate, cyanide, formate, hydroxide, hydrophosphite, phosphite, phosphate and derivatives, iodide, nitrate, sulphate, sulphite, aryl- and alkyl-sulphonates.

When the nickel compound used corresponds to an oxidation state of the nickel greater than 0, a reducing agent of the nickel is added to the reaction mixture, preferably reacting with it in the conditions of the reaction. This reducing agent can be organic or mineral. We may mention, as non-limiting examples, the borohydrides such as $BH_4Na$, $BH_4K$, Zn powder, magnesium or hydrogen.

When the nickel compound used corresponds to oxidation state 0 of the nickel, it is also possible to add a reducing agent such as those mentioned above, but said addition is not imperative.

When an iron compound is used, the same reducing agents are suitable. In the case of palladium, the reducing agent can be, additionally, elements of the reaction mixture (phosphine, solvent, olefin).

When the metal used is rhodium, for preparation of catalytic systems comprising compounds of general formula (I), (II), (III) or (IV), the complexes can be prepared using, as rhodium compounds, the compounds of the formula $(acac)Rh(CO)_2$ or $(acac)Rh(COD)$, in which:

acac denotes: acetylacetonate
COD denotes: cyclooctadiene

The present invention also relates to a method of hydrocyanation of olefins, more particularly of diolefins for the manufacture of nitrile compounds, more particularly of dinitrile compounds.

The organic compounds bearing at least one ethylenic double bond more particularly employed in the present method are diolefins such as butadiene, isoprene, hexadiene-1,5, cyclooctadiene-1,5, ethylenically unsaturated aliphatic nitriles, particularly the linear pentene-nitriles such as pentene-3-nitrile, pentene-4-nitrile as well as monoolefins such as styrene, methylstyrene, vinylnaphthalene, cyclohexene, methylcyclohexene as well as mixtures of several of these compounds.

The pentene-nitriles can contain, in addition to pentene-3-nitrile and pentene-4-nitrile, amounts, generally minor, of other compounds, such as methyl-2-butene-3-nitrile, methyl-2-butene-2-nitrile, pentene-2-nitrile, valeronitrile, adiponitrile, methyl-2-glutaronitrile, ethyl-2-succinonitrile or butadiene, resulting for example from the previous reaction of hydrocyanation of butadiene to unsaturated nitriles.

In fact, during the hydrocyanation of butadiene, there is formation, along with the linear pentene-nitriles, of non-negligible amounts of methyl-2-butene-3-nitrile and methyl-2-butene-2-nitrile.

The catalytic system used for the hydrocyanation according to the method of the invention can be prepared before it is fed into the reaction zone, for example by adding to the compound of formula (I), (II), (III) or (IV), alone or dissolved in a solvent, the appropriate amount of the selected transition metal compound and optionally of the reducing agent. It is also possible to prepare the catalytic system "in situ" simply by adding the compound of formula (I), (II), (III) or (IV) and the transition metal compound to the hydrocyanation reaction mixture before or after adding the compound that is to undergo hydrocyanation.

The amount of compound of nickel or of another transition metal used is selected to obtain a concentration in mol of transition metal per mol of organic compounds to undergo hydrocyanation or isomerization between $10^{-4}$ and 1, and preferably between 0.005 and 0.5 mol of nickel or of the other transition metal employed.

The amount of compound of formula (I), (II), (III) or (IV) used to form the catalyst is selected in such a way that the number of moles of this compound relative to 1 mol of transition metal is from 0.5 to 100 and preferably from 2 to 50.

Although the reaction is generally carried out without solvent, it may be advantageous to add an inert organic solvent. The solvent can be a solvent of the catalyst which is miscible with the phase comprising the compound that is to undergo hydrocyanation at the temperature of hydrocyanation. As examples of such solvents, we may mention aromatic, aliphatic or cycloaliphatic hydrocarbons.

The hydrocyanation reaction is generally carried out at a temperature from 10° C. to 200° C. and preferably from 30° C. to 120° C. It can be carried out in a single-phase medium.

The method of hydrocyanation of the invention can be used continuously or to discontinuously.

The hydrogen cyanide employed can be prepared from metal cyanides, notably sodium cyanide, or from cyanohydrins, such as acetone cyanohydrin or by any other known method of synthesis such as Andrussov's method consisting of reacting methane with ammonia and air.

Anhydrous hydrogen cyanide is fed into the reactor in the form of gas or liquid. It can also be dissolved beforehand in an organic solvent.

For discontinuous (batch) application, in practice a reactor, previously purged with an inert gas (such as nitrogen, argon), is charged either with a solution containing some or all of the various constituents such as the compound of formula I, II, III or IV, the transition metal (nickel) compound, the optional reducing agent and solvent, or with said constituents separately. Generally the reactor is then heated to the selected temperature, and then the compound that is to undergo hydrocyanation is introduced. The hydrogen cyanide itself is then introduced, preferably continuously and evenly.

When the reaction (the progress of which can be monitored by assaying samples) is completed, the reaction mixture is withdrawn after cooling and the reaction products are isolated and separated, for example by distillation.

Advantageously, the synthesis of dinitriles such as adiponitrile from diolefins (butadiene) is conducted in two successive stages. The first stage consists of hydrocyanation of a double bond of the diolefin to obtain an unsaturated mononitrile. The second stage consists of hydrocyanation of the unsaturation of the mononitrile to obtain the corresponding dinitrile or dinitriles. These two stages are generally implemented with a catalytic system comprising an organometallic complex of the same nature. However, the organophosphorus compound/metallic element ratios and the concentration of catalyst can be different. Moreover, it is preferable to combine the catalytic system with a cocatalyst or promoter in the second stage. This cocatalyst or promoter is generally a Lewis acid.

The Lewis acid used as cocatalyst notably makes it possible, in the case of hydrocyanation of ethylenically unsaturated aliphatic nitriles, to improve the linearity of the dinitriles obtained, i.e. the percentage of linear dinitrile relative to all of the dinitriles formed, and/or to increase the activity and the working life of the catalyst.

Lewis acid means, in the present text, according to the usual definition, compounds that are acceptors of electron doublets.

It is notably possible to use the Lewis acids mentioned in the work published by G. A. OLAH "Friedel-Crafts and related Reactions", Vol. I, pages 191 to 197 (1963).

The Lewis acids that can be employed as cocatalysts in the present method are selected from the compounds of the elements of groups Ib, IIb, IIIa, IIIb, IVa, IVb, Va, Vb, VIb, VIIb and VIII of the periodic system. Most often these compounds are salts, notably halides, such as chlorides or bromides, sulphates, sulphonates, halosulphonates, perhaloalkyl sulphonates, notably fluoroalkylsulphonates or perfluoroalkylsulphonates, carboxylates and phosphates.

As non-limiting examples of said Lewis acids, we may mention zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, chlorides or bromides of rare earth elements such as lanthanum, cerium, praseodymium, neodymium, samarium, europium, gadolinium, terbium, dysprosium, hafnium, erbium, thallium, ytterbium and lutetium, cobalt chloride, ferrous chloride, yttrium chloride.

It is also possible to use organometallic compounds as Lewis acid, such as triphenylborane, titanium isopropylate or the compounds described in the unpublished French patent application filed on 25 Jan. 2008 under No. 08 00381.

It is of course possible to use mixtures of several Lewis acids.

Among the Lewis acids, zinc chloride, zinc bromide, stannous chloride, stannous bromide, triphenylborane and zinc chloride/stannous chloride mixtures are quite particularly preferred.

The Lewis acid cocatalyst employed generally represents from 0.01 to 50 mol per mol of transition metal compound, more particularly of nickel compound, and preferably from 1 to 10 mol per mol.

The unsaturated mononitriles employed in this second stage are advantageously linear pentene-nitriles such as pentene-3-nitrile, pentene-4-nitrile and mixtures thereof.

These pentene-nitriles can contain amounts, generally minor, of other compounds, such as methyl-2-butene-3-nitrile, methyl-2-butene-2-nitrile, pentene-2-nitrile.

The catalytic solution used for hydrocyanation in the presence of Lewis acid can be prepared before it is fed into the reaction zone, for example by adding, to the compound of formula (I), (II), (III) or (IV), the appropriate amount of transition metal compound selected, of Lewis acid and optionally of reducing agent. It is also possible to prepare the catalytic solution "in situ" simply by adding these various constituents to the reaction mixture.

It is also possible, in the conditions of the method of hydrocyanation of the present invention, and notably by working in the presence of the catalytic system described previously comprising a compound of formula (I), (II), (III) or (IV) and at least one compound of a transition metal, to carry out, in the absence of hydrogen cyanide, the isomerization of methyl-2-butene-3-nitrile to pentenenitriles, and more generally of the branched unsaturated nitriles to linear unsaturated nitriles.

The methyl-2-butene-3-nitrile submitted to isomerization according to the invention can be employed alone or mixed with other compounds. Thus, it is possible to use methyl-2-butene-3-nitrile mixed with methyl-2-butene-2-nitrile, pentene-4-nitrile, pentene-3-nitrile, pentene-2-nitrile, butadiene.

It is particularly advantageous to treat the reaction mixture resulting from hydrocyanation of butadiene with HCN in the presence of at least one compound of formula (I), (II), (III) or (IV) and of at least one compound of a transition metal, more preferably a nickel compound with degree of oxidation 0, as defined previously. Within the scope of this preferred variant, as the catalytic system is already present for the reaction of hydrocyanation of butadiene, it is sufficient to stop all feed of hydrogen cyanide, to allow the isomerization reaction to take place.

In this variant it is possible, if necessary, to carry out a light purge of the reactor with an inert gas such as nitrogen or argon for example, in order to expel any hydrocyanic acid that might still be present.

The isomerization reaction is generally carried out at a temperature between 10° C. and 200° C. and preferably between 60° C. and 140° C.

In the preferred case of isomerization immediately following the reaction of hydrocyanation of butadiene, it will be advantageous to work at the temperature at which the hydrocyanation was carried out or slightly higher.

Just as for the method of hydrocyanation of ethylenically unsaturated compounds, the catalytic system used for isomerization can be prepared before it is fed into the reaction zone, for example by mixing the compound of formula (I), (II), (III) or (IV), with the appropriate amount of transition metal compound selected and optionally of reducing agent. It is also possible to prepare the catalytic system "in situ" simply by adding these various constituents to the reaction mixture. The amount of transition metal compound and more particularly of nickel used, as well as the amount of compound of formula (I), (II), (III) or (IV), are the same as for the reaction of hydrocyanation.

Although the isomerization reaction is generally carried out without solvent, it may be advantageous to add an inert organic solvent, which can be used subsequently as extractant. This is notably the case when such a solvent was employed in the reaction of hydrocyanation of butadiene, having been used for preparing the medium submitted to the isomerization reaction. Said solvents can be selected from those mentioned previously for hydrocyanation.

However, the preparation of dinitrile compounds by hydrocyanation of an olefin such as butadiene can be carried out using a catalytic system according to the invention for the stages of formation of the unsaturated nitriles and the aforementioned stage of isomerization, and the reaction of hydrocyanation of the unsaturated nitriles to dinitriles can be carried out with a catalytic system according to the invention or any other catalytic system already known for this reaction.

Similarly, the reaction of hydrocyanation of the olefin to unsaturated nitriles and the isomerization of the latter can be carried out with a catalytic system different from that of the invention, the stage of hydrocyanation of the unsaturated nitriles to dinitriles being carried out with a catalytic system according to the invention.

The invention also relates to a method of hydroformylation of alkenes for the synthesis of aldehydes.

The alkenes employed in the present method are, for example, linear olefins such as ethylene, propene, 1-butene, 1-pentene, 1-hexene, 1-octene.

In general the reaction of hydroformylation in the presence of a catalyst based on complexes of rhodium and of organophosphorus compounds is described, for example, in the article by J. FALBE, "New syntheses with carbon monoxide", Springer Verlag, Berlin, Heidelberg, N.Y., pages 95 ff. (1980). The olefins react with a $CO/H_2$ mixture (synthesis gas) in the presence of a catalyst. The reaction is carried out at temperatures between 40 and 180° C., preferably between 60° C. and 140° C., at a pressure between 1 and 300 bar, preferably between 10 and 70 bar. The CO/H$_2$ mixture (synthesis gas) has a volume ratio of hydrogen to carbon monoxide between 1 and 1.25. The catalyst and the ligand are dissolved in the hydroformylation medium, which can optionally include a solvent.

Other details and advantages of the invention will be illustrated by the examples given below, which are purely for illustration and are non-limiting.

EXAMPLES

Abbreviations Used

Ph: phenyl radical
Cod: cyclooctadiene
Ni(Cod)$_2$: bis(1,5-cyclooctadiene)nickel
Rh(acac)(CO)2: rhodium dicarbonyl acetylacetonate
3PN: 3-pentenenitrile
AdN: adiponitrile
ESN: ethylsuccinonitrile
MGN: methylglutaronitrile
DN: dinitrile compounds (AdN, MGN or ESN)
TIBAO: tetraisobutyldialuminoxane
TT(Y): degree of conversion of the product to be transformed Y corresponding to the ratio of the number of moles of Y transformed to the initial number of moles of Y
RR(DN): true yield of dinitriles corresponding to the ratio of the number of moles of dinitriles formed to the number of moles of 3PN used
Linearity (L): ratio of the number of moles of AdN formed to the number of moles of dinitriles formed (sum of the moles of AdN, ESN and MGN)

The following compounds: 3PN, Ni(Cod)$_2$, ZnCl$_2$, TIBAO, BPh$_3$, diphenylborinic anhydride (Ph$_2$BOPh$_2$), Rh(acac)(CO)$_2$ are known products and are commercially available.

Examples 1 to 10

Preparation of Ligands 1 to 10

In a first stage, a solution of Br$_2$ (3.5158 g, 0.022 mol) in CH$_2$Cl$_2$ (30 ml) is added in 30 minutes to a solution of CgPH (4.3243 g, 0.02 mol) in 60 ml of dichloromethane (CH$_2$Cl$_2$) at 0° C. and is stirred at this temperature for 30 minutes, then for one hour at room temperature. The solvent is evaporated and a slightly yellow solid is obtained (CgPBr). NMR $^{31}$P δ 53.5 (in CH$_2$Cl$_2$):

Compound CgPBr

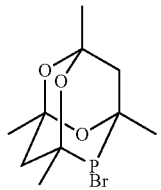

Manufacture of Ligand 1:
A solution of butyllithium (BuLi) in hexane (1.6 M, 0.02 mol, 12.5 ml) is slowly added to a solution of phenol (1.8822 g, 0.02 mol) in tetrahydrofuran (THF) (20 ml) at 0° C. The mixture is stirred for 1 hour at room temperature and then added in 30 min to a solution of CgPBr (5.9022 g, 0.02 mol) in THF (60 ml) at 0° C. The suspension obtained is stirred overnight prior to evaporation of the solvent. A solution of the raw ligand in CH$_2$Cl$_2$ is filtered on silica and the solvent is evaporated. The ligand is purified by silica column chromatography using a CH$_2$Cl$_2$/pentane mixture (⅓ by volume) as solvent, under nitrogen pressure.
Amount obtained: 4.33 g (yield: 70%)
$^{31}$P NMR δ 79.3 (in CDCl$_3$)

Manufacture of Ligand 2:
A solution of BuLi in hexane (1.6 M, 0.02 mol, 12.5 ml) is slowly added to a solution of 2,4,6-trimethylphenol (2.7238 g, 0.02 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$, filtered and the solvent is evaporated. The ligand is purified by silica column chromatography using a CH$_2$Cl$_2$/pentane mixture (⅓ by volume) as solvent, under nitrogen pressure.
Amount obtained: 4.21 g (60%)
$^{31}$P NMR δ 82.0 (in CDCl$_3$)

Manufacture of Ligand 3:
A solution of BuLi in hexane (1.6 M, 0.02 mol, 12.5 ml) is slowly added to a solution of 2-methylphenol (2.1628 g, 0.02 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$, filtered and the solvent is evaporated. The ligand is purified by silica column chromatography using a CH$_2$Cl$_2$/pentane mixture (⅓ by volume) as solvent, under nitrogen pressure.
Amount obtained: 5.01 g (78%)
$^{31}$P NMR δ 76.0 (in CDCl$_3$)

Manufacture of Ligand 4:
A solution of BuLi in hexane (1.6 M, 0.02 mol, 12.5 ml) is slowly added to a solution of 2,4-di-tert-butylphenol (4.125 g, 0.02 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$, filtered and the solvent is evaporated. The ligand is purified by silica column chromatography using a CH$_2$Cl$_2$/pentane mixture (⅓ by volume) as solvent, under nitrogen pressure.
Amount obtained: 6.24 g (74%)
$^{31}$P NMR δ 68.8 (in CDCl$_3$)

Manufacture of Ligand 5
A solution of BuLi in hexane (1.6 M, 0.02 mol, 12.5 ml) is slowly added to a solution of diphenol (1.8621 g, 0.01 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$ and filtered and the solvent is evaporated. Ligand 5 is purified by recrystallization from a CH$_2$Cl$_2$/pentane mixture (⅓ by volume).

Amount obtained: 3.0 g (49%)
31P NMR δ 82.8 (in CDCl$_3$)

Manufacture of Ligand 6:

A solution of BuLi in hexane (1.6 M, 0.02 mol, 12.5 ml) is slowly added to a solution of methanol (0.5768 g, 0.018 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$, filtered and the solvent is evaporated. The ligand is purified by silica column chromatography using a CH$_2$Cl$_2$/pentane mixture (⅓ by volume) as solvent, under nitrogen pressure.

Amount obtained: 3.11 g (70%)
$^{31}$P NMR δ 88.5 (in CDCl$_3$)

Manufacture of Ligand 7:

A solution of BuLi in hexane (1.6 M, 0.02 mol, 12.5 ml) is slowly added to a solution of 1,2-benzenedimethanol (1.2711 g, 0.00092 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The raw ligand is dissolved in CH$_2$Cl$_2$ (60 ml) and 50 ml of water is added. The aqueous phase is extracted with CH$_2$Cl$_2$ (50 ml) and the combined organic phases are dried over Na$_2$SO$_4$, filtered and the solvent is evaporated. The ligand is purified by silica column chromatography using an ethyl acetate/hexane mixture (⅙ by volume) as solvent, under nitrogen pressure.

Amount obtained: 3.87 g (74%)
$^{31}$P NMR δ 85.9 and 86.0 (in CDCl$_3$)

Manufacture of Ligand 8:

A solution of BuLi in hexane (1.6 M, 0.02 mol, 12.5 ml) is slowly added to a solution of trifluoroethanol (2.0008 g, 0.02 mol) in THF (20 ml) at 0° C. The mixture is stirred for 1 hour at room temperature and is then added in 30 min to a solution of CgPBr (5.9022 g, 0.02 mol) in THF (60 ml) at 0° C. The suspension obtained is stirred overnight prior to evaporation of the solvent. The ligand is purified by silica column chromatography using a CH$_2$Cl$_2$/pentane mixture (⅓ by volume) as solvent, under nitrogen pressure.

Amount obtained: 4.81 g, (77%).
$^{31}$P NMR δ 97.2, $^4J_{P,F}$ 7.4 Hz (in CDCl$_3$)
$^{19}$F NMR δ −75.1, $^4J_{F,P}$≈$^3J_{F,H}$ 7.3 Hz (in CDCl$_3$)

Manufacture of Ligand 9:

A solution of BuLi in hexane (1.6 M, 0.01 mol, 6.25 ml) is slowly added to a solution of 1,2-benzene(dimethanol) (2.0725 g, 0.015 mol) in THF (50 ml) at 0° C. The mixture is brought slowly to room temperature and stirred for 1 hour. A solution of CgPBr (2.9511 g, 0.01 mol) in THF (50 ml) is then slowly added to the above suspension at 0° C. in 30 minutes and the mixture is stirred for 3 hours at room temperature. The solvent is evaporated, the solid obtained is dissolved in CH$_2$Cl$_2$ (50 ml) and 50 ml of water is added. The aqueous phase is extracted with 50 ml of CH$_2$Cl$_2$ and the combined organic phases are dried over Na$_2$SO$_4$, filtered and the solvent is evaporated. The compound is purified by silica column chromatography using an ethyl acetate/hexane mixture (⅙ by volume) as solvent, under nitrogen pressure.

Amount obtained: 2.89 g (yield 82%)
$^{31}$P NMR δP 87.9 (CDCl$_3$)

Manufacture of Ligand 10:

A solution of butyllithium (BuLi) in hexane (1.6 M, 0.01 mol, 6.25 ml) is slowly added to a solution of thiophenol (1.11 g, 0.01 mol) in tetrahydrofuran (THF) (15 ml) at 0° C. The mixture is stirred for 1 hour at room temperature and is then added in 30 min to a solution of CgPBr (2.95 g, 0.01 mol) in THF (50 ml) at 0° C. The suspension obtained is stirred overnight prior to evaporation of the solvent. The ligand is purified by silica column chromatography using a CH$_2$Cl$_2$/pentane mixture (⅓ by volume) as solvent, under nitrogen pressure.

Amount obtained: 2.76 g (85%)
31P NMR δP 21.5 (CDCl$_3$)

Examples 11 to 15

Hydroformylation of 1-hexene

The following general procedure is used:

Under an inert atmosphere, an autoclave is charged with Rh(acac)(CO)$_2$ (6.2 mg, 0.024 mmol), the ligand according to the invention, the nature and amount of which are shown in Table I, and 5 ml of toluene. The reactor is then pressurized with an H$_2$/CO mixture (1:1, molar ratio) at 20 bar and is heated to 60° C. for 1 hour, and then cooled to room temperature, depressurized and purged with nitrogen. 1.2 ml of 1-hexene is then added and the autoclave is pressurized again with H$_2$/CO mixture (1:1, molar ratio) at 20 bar and heated to 60° C. for 1 hour. The reactor is then cooled to room temperature, depressurized and purged with nitrogen. The product obtained is analysed by $^1$H NMR (analysis by nuclear magnetic resonance). The product obtained is a mixture comprising the products resulting from hydroformylation, such as: heptanal (linear product) and 2-methylhexanal (branched product).

The results are presented in Table I below:

TABLE I

Examples 11 to 15

| example | ligand | Ligand/Rh (molar) | TT (1-hexene) | Linear/branched product (mol. %) |
|---|---|---|---|---|
| 11 | 1 | 4.5 | 100 | 60/40 |
| 12 | 2 | 4.5 | 100 | 65/35 |
| 13 | 3 | 4.5 | 100 | 62/38 |
| 14 | 4 | 4.5 | 100 | 66/34 |
| 15 | 6 | 4.5 | 63 | 59/41 |

Examples 16 to 30

Hydrocyanation of 3-PN to AdN

The following general procedure is used:

Under an argon atmosphere, a 60-ml tube of Schott type glass equipped with a stopper-septum is charged successively with:
  the ligand (1 mmol, 2 equivalents in P)
  1.21 g (15 mmol, 30 equivalents) of anhydrous 3PN
  138 mg (0.5 mmol, 1 equivalent) of Ni(cod)$_2$
  Lewis acid (see Table 2 for amount)

The mixture is stirred at 70° C. Acetone cyanohydrin is injected into the reaction mixture with a syringe pump at a flow rate of 0.45 ml per hour. After injection for 3 hours, the syringe pump is stopped. The mixture is cooled to room temperature, diluted with acetone and analysed by gas chromatography.

The results are presented in the following table:

TABLE II

Examples 16 to 30

| example | ligand | Lewis acid | Lewis acid/Ni (molar) | Linearity | RR (DN) |
|---|---|---|---|---|---|
| 16 | 1 | Ph$_2$BOBPh$_2$ | 0.5 | 73.1 | 3.2 |
| 17 | 5 | ZnCl$_2$ | 1 | 99 | 1.3 |
| 18 | 5 | BPh$_3$ | 1 | 69.8 | 4.4 |
| 19 | 5 | Ph$_2$BOBPh$_2$ | 0.5 | 79 | 4.5 |
| 20 | 6 | BPh$_3$ | 1 | 67 | 4.6 |
| 21 | 6 | Ph$_2$BOBPh$_2$ | 0.5 | 78.7 | 7.4 |
| 22 | 6 | TIBAO | 0.5 | 64.2 | 18.5 |
| 23 | 7 | ZnCl$_2$ | 1 | 74.7 | 39.9 |
| 24 | 7 | Ph$_2$BOBPh$_2$ | 0.5 | 73.2 | 5.9 |
| 25 | 8 | Ph2BOBPh2 | 0.5 | 75.1 | 15.2 |
| 26 | 8 | TIBAO | 0.5 | 60.8 | 36.3 |
| 27 | 9 | ZnCl$_2$ | 1 | 93.7 | 0.8 |
| 28 | 9 | TIBAO | 2 | 71 | 6.8 |
| 29 | 10 | ZnCl$_2$ | 1 | 100 | 0.6 |
| 30 | 10 | TIBAO | 0.5 | 74 | 0.8 |

The invention claimed is:

1. An organophosphorus compound, wherein the compound has the formula (I) or (II):

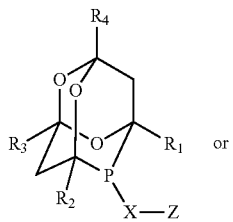

(I)

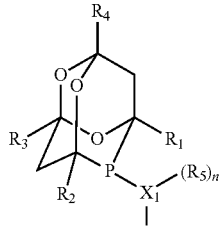

(II)

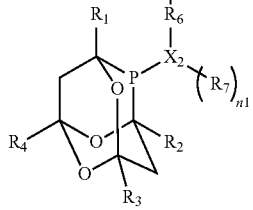

in which:

$R_1$, $R_2$, $R_3$, $R_4$, $R_5$, $R_7$ and Z, which can be identical or different, represent a hydrogen atom; a linear or branched alkyl radical having from 1 to 12 carbons which can comprise heteroatoms; a radical comprising a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

X, X1 and X2, which can be identical or different, represent an oxygen, nitrogen, sulphur, or silicon atom;

$R_6$ represents a covalent bond; a linear or branched aliphatic radical; a radical comprising a substituted or unsubstituted aromatic or cycloaliphatic ring; or several aromatic rings, condensed or joined together by a bond; and n and n1, which can be identical or different, are integers respectively equal to the valency of elements $X_1$ and $X_2$ reduced by 2.

2. The compound according to claim 1, wherein the compound has formula (III) or (IV):

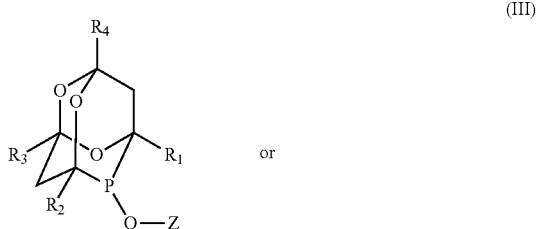

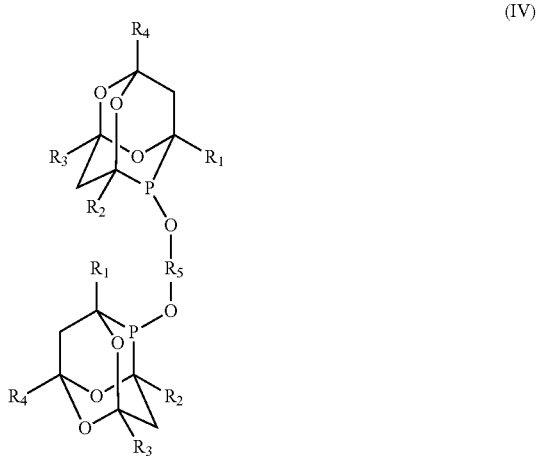

in which:

$R_1$, $R_2$, $R_3$, and $R_4$, which can be identical or different, represent a hydrogen atom; or a linear or branched alkyl radical having from 1 to 12 carbon atoms which can comprise heteroatoms;

Z represents a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

$R_5$ represents a covalent bond; a linear or branched aliphatic radical; a radical comprising a substituted or unsubstituted aromatic or cycloaliphatic ring; or several aromatic rings, condensed or joined together by a bond.

3. The compound according to claim 1, wherein the compound is selected from the group consisting of compounds having the following formulae:

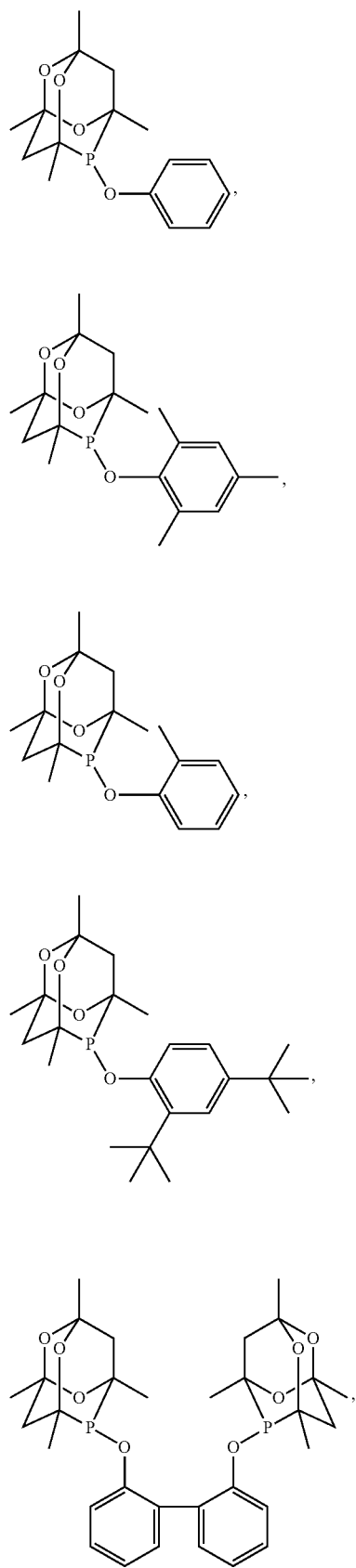
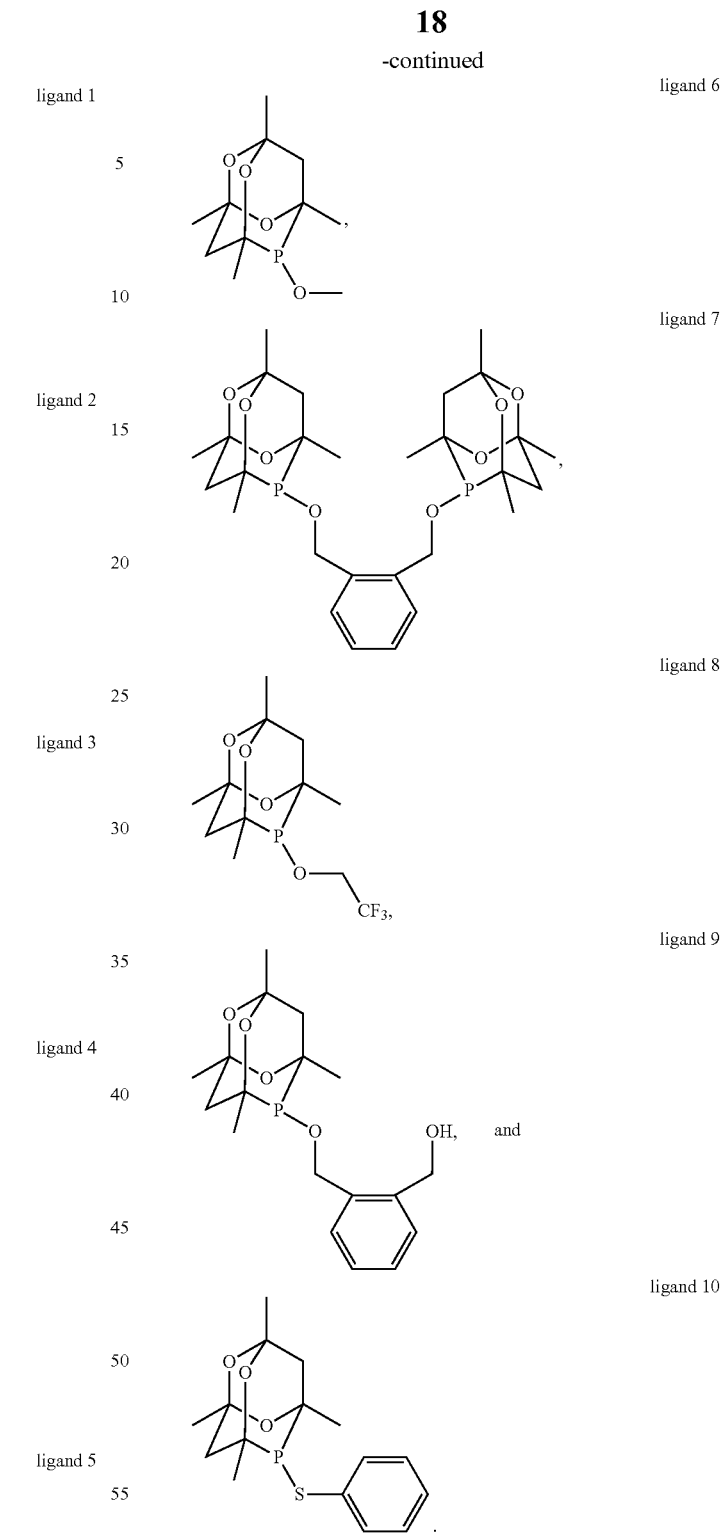
4. A catalytic system comprising a metallic element (M) forming a complex with an organophosphorus compound, wherein the complex has the following formula (V) or (VI):
$$M[L_f]_t \quad (V)$$
$$HM[L_f]_{t+n2}CO_{4-n2} \quad (VI)$$
in which:
M is a transition metal;

$L_f$ represents at least one organophosphorus compound having formula (I), (II), (III) or (IV);

t represents a number between 1 and 10 (inclusive); and n2 represents a number between 1 and 4 (inclusive);

wherein formula (I) or (II) is:

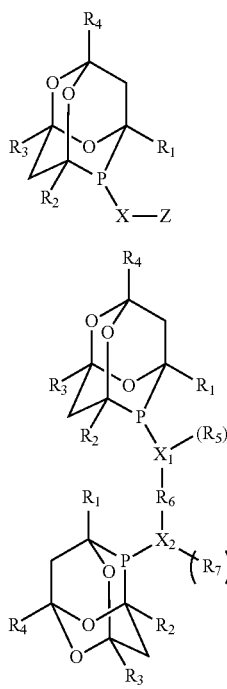

in which:

$R_1$, $R_2$, $R_3$, $R_4$, $R_5$, $R_7$ and Z, which can be identical or different, represent a hydrogen atom; a linear or branched alkyl radical having from 1 to 12 carbons which can comprise heteroatoms; a radical comprising a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

X, X1 and X2, which can be identical or different, represent an oxygen, nitrogen, sulphur, or silicon atom;

$R_6$ represents a covalent bond; a linear or branched aliphatic radical; a radical comprising a substituted or unsubstituted aromatic or cycloaliphatic ring; or several aromatic rings, condensed or joined together by a bond; and n and n1, which can be identical or different are integers respectively equal to the valency of elements $X_1$ and $X_2$ reduced by 2; and wherein formula (III) or (IV) is:

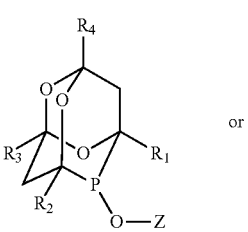

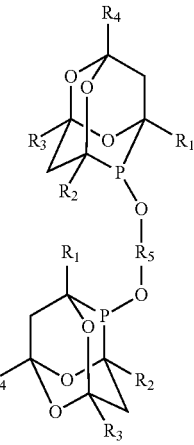

in which:

$R_1$, $R_2$, $R_3$, $R_4$, which can be identical or different, represent a hydrogen atom; or a linear or branched alkyl radical having from 1 to 12 carbon atoms which can comprise heteroatoms;

Z represents a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

$R_5$ represents a covalent bond; a linear or branched aliphatic radical; a radical comprising a substituted or unsubstituted aromatic or cycloaliphatic ring; or several aromatic rings, condensed or joined together by a bond.

5. The system according to claim 4, wherein the metallic element (M) is selected from the group consisting of nickel, cobalt, iron, ruthenium, rhodium, palladium, osmium, iridium, platinum, copper, silver, gold, zinc, cadmium, and mercury.

6. A method of hydrocyanation of a hydrocarbon compound, the method comprising reacting a hydrocarbon compound comprising at least one ethylenic unsaturation, in a liquid medium with hydrogen cyanide in the presence of the catalytic system according to claim 4, wherein the metallic element (M) is nickel.

7. The method according to claim 6, wherein the hydrocarbon compound comprising at least one ethylenic unsaturation is selected from the group consisting of a diolefin, an ethylenically unsaturated aliphatic nitrile, a monoolefin, and a mixture of these compounds.

8. The method according to claim 6, wherein the amount of nickel compound is between $10^{-4}$ and 1 mol per mol of the hydrocarbon compound comprising at least one ethylenic unsaturation and the amount of organophosphorus compounds used is from 0.5 to 100 mol to 1 mol of nickel.

9. The method according to claim 6, wherein the hydrocarbon compound is an ethylenically unsaturated nitrile compound and wherein the hydrocyanation is carried out in the presence of the catalytic system comprising nickel, and at least one organophosphorus compound of formula (I) (II), (III) or (IV) and further comprising at least one Lewis acid as a cocatalyst;

wherein formula (I) or (II) is:

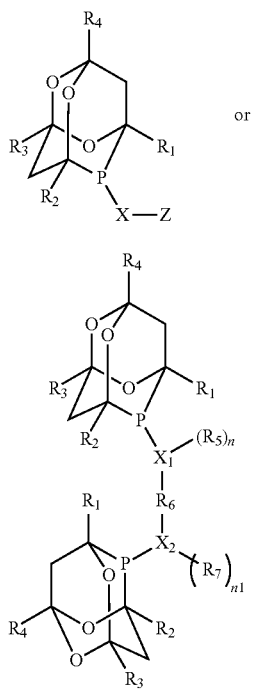

in which:
R₁, R₂, R₃, R₄, R₅, R₇ and Z, which can be identical or different, represent a hydrogen atom; a linear or branched alkyl radical having from 1 to 12 carbons which can comprise heteroatoms; a radical comprising a substituted or unsubstituted aromatic or cycloaliphatic radical which can comprise heteroatoms, a carbonyl, alkoxycarbonyl or alkoxy radical, a halogen atom; a nitrile group; or a haloalkyl group having 1 to 12 carbon atoms;

X, X1 and X2, which can be identical or different, represent an oxygen, nitrogen, sulphur, or silicon atom;

R₆ represents a covalent bond; a linear or branched aliphatic radical; a radical comprising a substituted or unsubstituted aromatic or cycloaliphatic ring; or several aromatic rings, condensed or joined together by a bond; and n and n1, which can be identical or different, are integers respectively equal to the valency of elements X₁ and X₂ reduced by 2; and wherein formula (III) or (IV) is:

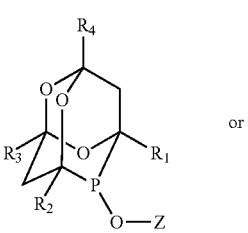

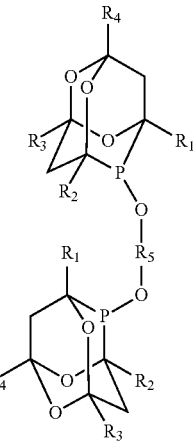

in which:
R₁, R₂, R₃, and R₄, which can be identical or different, represent a hydrogen atom; or a linear or branched alkyl radical having from 1 to 12 carbon atoms which can comprise heteroatoms;

Z represents a substituted or unsubstituted aromatic or cycloaliphatic radical which can comprise heteroatoms, a carbonyl, alkoxycarbonyl or alkoxy radical; a halogen atom; a nitrile group; or a haloalkyl croup having 1 to 12 carbon atoms;

R₅ represents a covalent bond; a linear or branched aliphatic radical; a radical comprising a substituted or unsubstituted aromatic or cycloaliphatic ring; or several aromatic rings, condensed or joined together by a bond.

10. The method according to claim 9, wherein the ethylenically unsaturated nitrile compound is an ethylenically unsaturated aliphatic nitrile.

11. The method according to claim 9, wherein the Lewis acid is a compound comprising an element selected from the group consisting of group Ib, group IIb, group IIIa, group IIIb, group IVa, group IVb, group Va, group Vb, group VIb, group VIIb and group VIII of the periodic table.

12. The method according to claim 9, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulphate, stannous tartrate, indium trifluoromethylsulphonate, rare earth element of chloride or bromide, cobalt chloride, ferrous chloride, yttrium chloride, organometallic compounds, and mixtures thereof.

13. A method of hydroformylation of alkenes, wherein the method comprises reacting alkenes with a mixture of carbon monoxide (CO) and hydrogen (H₂) in the presence of the catalytic system according to claim 4, wherein the metallic element (M) is rhodium or cobalt.

14. The method according to claim 7, wherein the diolefin is selected from the group consisting of butadiene, isoprene, hexadrene-1,5, and cyclooctadiene-1,5.

15. The method according to claim 7, wherein the ethylenically unsaturated aliphatic nitrile is a linear pentenenitrile.

16. The method according to claim 15, wherein the linear pentenenitrile is pentene-3-nitrile or pentene-4-nitrile.

17. The method according to claim 7, wherein the monoolefin is selected from the group consisting of styrene, methylstytrene, vinylnaphthalene, and cyclohexene.

18. The method according to claim 10, wherein the ethylenically unsaturated aliphatic nitrile is a linear pentenenitrile.

19. The method according to claim 18, wherein the linear pentenenitrile is pentene-3-nitrile or pentene-4-nitrile or a mixture thereof.

20. The method according to claim 12, wherein the rare earth element is selected from the group consisting of lanthanum, cerium, praseodymium, neodymium, samarium, europium, gadolinium, terbium, dysprosium, hafnium, erbium, thallium, ytterbium, and lutetium.

21. A method of isomerization of an unsaturated nitrile to a linear unsaturated nitrile, the method comprises isomerizing an unsaturated nitrile in the absence of hydrogen cyanide and in the presence of the catalytic system according to claim 4.

22. The method of isomerization according to claim 21, wherein the unsaturated nitrile is methyl-2-butene-3-nitrile and wherein the linear nitrile is pentenenitrile.

23. A method of hydrocyanation of a hydrocarbon compound, the method comprising reacting a hydrocarbon compound comprising at least one ethylenic unsaturation, in a liquid medium with hydrogen cyanide in the presence of the catalytic system according to claim 4 to form methyl-2-butene-3-nitrile, wherein the metallic element (M) is nickel, and isomerizing methyl-2-butene-3-nitrile in the absence of hydrogen cyanide and in the presence of a catalyst bearing at least one compound of formula (I) (II), (III) or (IV) and at least one compound of a transition metal wherein formula (I) or (II) is:

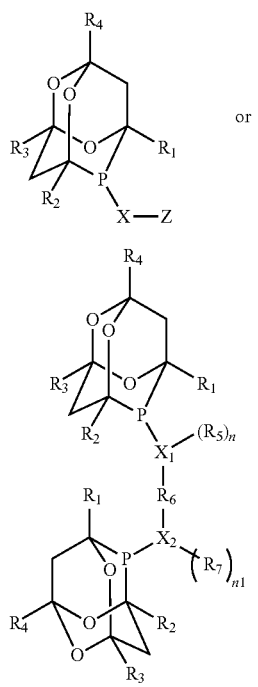

in which:

$R_1$, $R_2$, $R_3$, $R_4$, $R_5$, $R_7$ and Z, which can be identical or different, represent a hydrogen atom; a linear or branched alkyl radical having from 1 to 12 carbons which can comprise heteroatoms; a radical comprising a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

X, X1 and X2, which can be identical or different, represent an oxygen, nitrogen, sulphur, or silicon atom;

$R_6$ represents a covalent bond; a linear or branched aliphatic radical; a radical comprising a substituted or unsubstituted aromatic or cycloaliphatic ring; or several aromatic rings, condensed or joined together by a bond; and n and n1, which can be identical or different, are integers respectively equal to the valency of elements $X_1$ and $X_2$ reduced by 2; and wherein formula (III) or (IV) is:

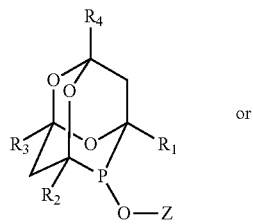

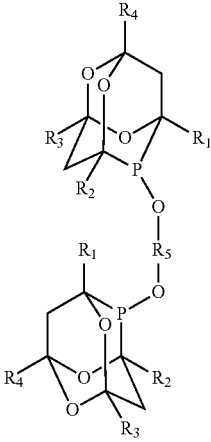

in which:

$R_1$, $R_2$, $R_3$, and $R_4$, which can be identical or different, represent a hydrogen atom; or a linear or branched alkyl radical having from 1 to 12 carbon atoms which can comprise heteroatoms;

Z represents a substituted or unsubstituted aromatic or cycloaliphatic radical which can comprise heteroatoms, a carbonyl, alkoxycarbonyl or alkoxy radical; a halogen atom; a nitrile group; or a haloalkyl group having 1 to 12 carbon atoms;

$R_5$ represents a covalent bond; a linear or branched aliphatic radical; a radical comprising a substituted or unsubstituted aromatic or cycloaliphatic ring; or several aromatic rings, condensed or joined together by a bond.

* * * * *